United States Patent [19]

Sato et al.

[11] Patent Number: 4,495,188
[45] Date of Patent: Jan. 22, 1985

[54] ACYLAMINOQUINAZOLINE DERIVATIVES AND A PHARMACEUTICAL COMPOSITION CONTAINING THEM

[75] Inventors: Yasunobu Sato; Hiroshi Fukumi; Hiroyuki Koike; Nobuaki Kitahara, all of Tokyo, Japan

[73] Assignee: Sankyo Company Limited, Tokyo, Japan

[21] Appl. No.: 324,425

[22] Filed: Nov. 24, 1981

[30] Foreign Application Priority Data

Nov. 26, 1980 [JP] Japan .................. 55-166327

[51] Int. Cl.³ .................. A61K 31/505; C07D 403/14; C07D 417/14
[52] U.S. Cl. .................. 514/260; 544/284; 544/291; 260/243.3; 514/218
[58] Field of Search .................. 544/291, 284; 424/251; 260/243.3; 542/431, 436

[56] References Cited

U.S. PATENT DOCUMENTS

| | | | |
|---|---|---|---|
| 3,511,836 | 5/1970 | Hess | 544/291 |
| 3,574,212 | 4/1971 | Hess | 544/291 |
| 3,971,783 | 7/1976 | Barnish et al. | 544/284 |
| 4,001,237 | 1/1977 | Partyka et al. | 544/291 |
| 4,001,238 | 1/1977 | Partyka et al. | 544/291 |
| 4,062,844 | 12/1977 | Hammen | 544/291 |
| 4,128,643 | 12/1978 | Merkel et al. | 544/281 |

OTHER PUBLICATIONS

Morrison, et al., *Organic Chemistry*, Sec. Ed., 1966, Allyn and Bacon, Inc., pp. 589–593.

*Primary Examiner*—Glennon H. Hollrah
*Assistant Examiner*—James H. Turnipseed
*Attorney, Agent, or Firm*—Frishauf, Holtz, Goodman & Woodward

[57] ABSTRACT

Acylaminoquinazoline derivatives of formula

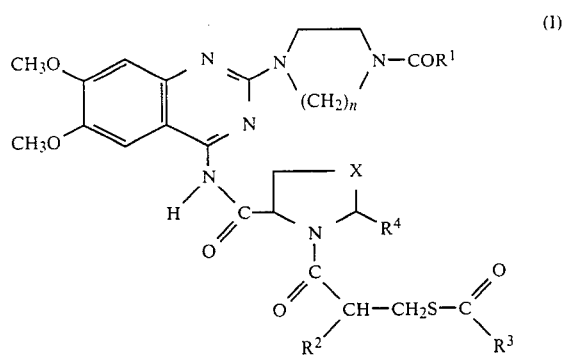

(in which:

$R^1$ represents a lower alkoxy group, a substituted or unsubstituted lower alkyl group, a cycloalkyl group, a lower alkenyl group, a vinyl group having an optionally substituted phenyl or furyl substituent, an optionally substituted phenyl group, a furyl group, an oxazolyl group, a methylthiooxadiazolyl group or a tetrahydrofuryl group;

$R^2$ represents a hydrogen atom or a lower alkyl group;

$R^3$ represents a lower alkyl group or an optionally substituted phenyl group;

$R^4$ represents a hydrogen atom or an acyloxy-substituted phenyl group;

X represents a methylene group or a sulphur atom; and n is 2 or 3)

and pharmaceutically acceptable acid addition salts thereof are valuable antihypertensive agents and inhibit the activity of the angiotension I-converting enzyme. They may be prepared by reacting a 4-aminoquinazoline derivative with a carboxylic acid or reactive derivative thereof corresponding to the amide group which it is desired to introduce at the 4- position of said compound of formula (I). The compounds of the invention may be formulated with conventional pharmaceutically acceptable carriers or diluents to provide a pharmaceutical composition.

20 Claims, No Drawings

ACYLAMINOQUINAZOLINE DERIVATIVES AND A PHARMACEUTICAL COMPOSITION CONTAINING THEM

BACKGROUND OF THE INVENTION

The present invention relates to a series of novel acylaminoquinazoline derivatives having valuable antihypertensive activities, to a process for preparing these derivatives and to pharmaceutical compositions containing these derivatives.

A variety of quinazoline derivatives, including some piperazinyl- and homopiperazinyl-quinazoline derivatives, are known and many of these are known to have hypotensive (or antihypertensive) activity. For example, various such derivatives are described in U.S. Pat. Nos. 3,511,836, 4,060,615, and 3,920,636 and a number of these compounds have been proposed for use as hypotensive agents, and similar compounds are described in copending U.S. application Ser. No. 233,679, filed Feb. 11, 1981, now U.S. Pat. No. 4,426,382 by Y. Sato et al.

In practice, however, only one of these known quinazoline derivatives has actually been used. This compound, which is one of the compounds disclosed in U.S. Pat. No. 3,511,836, is known by the name "prazosin" and has the formula:

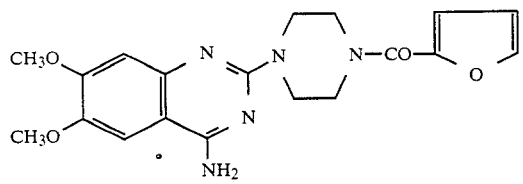

Cushman et al. [Science, 196, 441 (1977)] have reported that 1-(D-3-mercapto-2-methylpropanoyl)-L-proline, which, of course, belongs to a wholly different class of compound from the quinazoline derivatives discussed above, shows potent inhibitory activity against the angiotensin I-converting enzyme and, as a result of this inhibitory activity, exhibits antihypertensive activity in hypertensive animals.

Accordingly, we have investigated the possibility of combining the antihypertensive activity characteristic of the piperazinyl- and homopiperazinyl-quinazoline derivatives discussed above with the angiotensin I-converting enzyme inhibitory activity characteristic of 1-(D-3-mercapto-2-methylpropanoyl)-L-proline. In piperazinyl- and homopiperazinyl-quinalzoline derivatives where the nitrogen atom at the 4- position of the piperazine or homopiperazine ring is unsubstituted, reacting the quinazoline derivative with the proline derivative results in acylation of the quinazoline derivative both at the nitrogen atom of the piperazone or homopiperazine ring and at the free amino group which is normally present on the 4- position of the quinazoline system. Accordingly, we have found that, in order to achieve an active compound, it is necessary that the nitrogen atom in the 4- position of the piperazine or homopiperazine ring should be protected; we have also found that the most satisfactory compounds are produced using different proline derivatives from the 1-(D-3-mercapto-2-methylpropanoyl)-L-proline referred to above.

BRIEF SUMMARY OF THE INVENTION

The acylaminoquinazoline derivatives of the present invention are those compounds of formula (I):

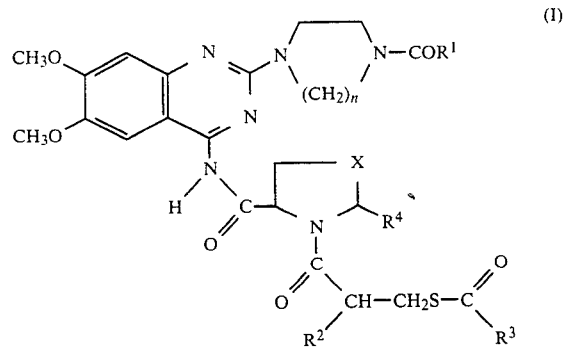

in which:

$R^1$ represents a lower alkoxy group, a lower alkyl group, a cycloalkyl group, a lower alkenyl group, a vinyl group having a furyl or phenyl substituent (which phenyl substituent may itself be unsubstituted or have one or more lower alkoxy or methylenedioxy substituents), an alkyl group having a phenyl, phenoxy or cycloalkylidene substituent, a phenyl group which is unsubstituted or has one or more lower alkoxy or phenyl-substituted lower alkoxy substituents, a furyl group, an oxazolyl group, a methylthiooxadiazolyl group or a tetrahydrofuryl group;

$R^2$ represents a hydrogen atom or a lower alkyl group;

$R^3$ represents a lower alkyl group or a phenyl group which is unsubstituted or has one or more lower alkyl, lower alkoxy or halogen substituents;

$R^4$ represents a hydrogen atom or an acyloxy-substituted phenyl group;

X represents a methylene group or a sulphur atom; and n represents 2 or 3.

The invention also provides pharmaceutically acceptable acid addition salts of said compounds of formula (I).

It is also an object of the invention to provide a process for the preparation of said compounds of formula (I) and salts thereof.

It is a still further object of the invention to provide a pharmaceutical composition comprising, as active ingredient, one or more of the compounds of formula (I) or salts thereof in admixture with a pharmaceutically acceptable carrier or diluent.

The term "lower alkyl group" as used herein means an alkyl group having from 1 to 6 carbon atoms and the terms "lower alkoxy" and "lower alkenyl" are to be construed accordingly as referring to such groups having no more than 6 carbon atoms.

DETAILED DESCRIPTION OF INVENTION

In the compounds of formula (I) where $R^1$ represents a lower alkoxy group, this may be a straight or branched chain group and preferably has from 1 to 4 carbon atoms; examples of such groups include the methoxy, ethoxy, propoxy, isopropoxy, butoxy or t-butoxy groups.

Where $R^1$ represents a lower alkyl group, this may be a straight or branched chain group and it preferably has from 1 to 5 carbon atoms; examples of such groups include the methyl, ethyl, propyl, isopropyl, butyl, t-butyl and pentyl groups.

Where $R^1$ represents a cycloalkyl group, this preferably has from 3 to 7 carbon atoms and examples of such groups include the cyclopropyl, cyclobutyl, cyclopentyl, cyclohexyl and cycloheptyl groups.

Where $R^1$ represents a lower alkenyl group, this may be a straight or branched chain group and it preferably has from 2 to 5 carbon atoms. Examples of such groups include the vinyl, isopropenyl, 1-propenyl, allyl, 1-ethylvinyl, 1-butenyl, 2-butenyl, 3-butenyl, 2-methyl-1-propenyl, 1-methyl-1-propenyl, 2-methylallyl, 1-propylvinyl, 1-pentenyl, 2-pentenyl, 3-pentenyl, 4-pentenyl, 1-methyl-1-butenyl, 2-methyl-1-butenyl, 3-methyl-2-butenyl, 1-methyl-3-butenyl, 2-methyl-2-butenyl and 1,1-dimethyl-2-propenyl groups.

Where $R^1$ represents a vinyl group having a phenyl or furyl substituent, the phenyl group may be substituted or unsubstituted and the furyl group may be a 2-furyl or 3-furyl group. The optional substituents on the phenyl group may be straight or branched chain lower alkoxy groups, preferably having from 1 to 3 carbon atoms (e.g. methoxy, ethoxy, propoxy or isopropoxy groups), or a methylenedioxy group. The phenyl group may have a single such substituent or it may have two or more such substituents.

Where $R^1$ represents an alkyl group having a cycloalkylidene, a phenyl or phenoxy substituent, the alkyl group is preferably a lower alkyl group and more preferably an alkyl group, which may be straight or branched chain, having from 1 to 3 carbon atoms. The cycloalkylidene substituent preferably has from 3 to 7 carbon atoms and examples of such cycloalkylidenealkyl groups include the cyclopropylidenemethyl, cyclobutylidenemethyl, cyclopentylidenemethyl, cyclohexylidenemethyl and cycloheptylidenemethyl groups. Examples of alkyl groups having phenyl or phenoxy substituents include the benzyl, 1-phenylethyl, 2-phenylethyl, phenoxymethyl, 1-phenoxyethyl, 2-phenoxyethyl and 1-methyl-1-phenoxyethyl groups.

Where $R^1$ represennts a phenyl group, this may be unsubstituted or may have one or more substituents selected from unsubstituted alkoxy groups and phenyl-substituted alkoxy groups. The unsubstituted alkoxy groups, which may be straight or branched chain groups, preferably have from 1 to 4 carbon atoms and examples include the methoxy, ethoxy, propoxy, isopropoxy and butoxy groups. The phenyl-substituted alkoxy groups preferably have from 1 to 3 carbon atoms in the alkoxy moiety, which may be straight or branched chain, and examples include the benzyloxy, 1-phenylethoxy, 2-phenylethoxy and 1-methyl-1-phenylethoxy groups.

$R^1$ may also represent a furyl group (2-furyl or 3-furyl), an oxazolyl group (e.g. 4-oxazolyl or 5-oxazolyl), a methylthiooxadiazolyl group (e.g. 5-methylthio-1,3,4-oxadiazolyl) or a tetrahydrofuryl group (2-tetrahydrofuryl or 3-tetrahydrofuryl).

Where $R^2$ represents a lower alkyl group, this may be a straight or branched chain group and preferably is a group having from 1 to 3 carbon atoms, e.g. a methyl, ethyl, propyl or isopropyl group.

Where $R^3$ represents a lower alkyl group, this may be a straight or branched chain group and is preferably a $C_1$–$C_5$ alkyl group, for example a methyl, ethyl, propyl, isopropyl, butyl, isobutyl, t-butyl or pentyl group.

Where $R^3$ represents a phenyl group, this may be unsubstituted or may have one or more lower alkyl (e.g. methyl, ethyl, propyl, isopropyl, butyl, isobutyl, t-butyl or pentyl), lower alkoxy (e.g. methoxy, ethoxy, propoxy or isopropoxy) or halogen (e.g. fluorine, chlorine or bromine) substituents.

Where $R^4$ represents a phenyl group having an acyloxy substituent, this acyloxy group may be a straight or branched chain group and preferably has from 2 to 4 carbon atoms; examples of such acyloxy groups include the acetoxy, propanoyloxy and 2-methylpropanoyloxy groups.

A preferred class of compounds of the invention are those compounds in which:

$R^1$ represents a lower alkoxy group, a lower alkenyl group, an alkyl group having a phenyl or phenoxy substituent, a phenyl group having a lower alkoxy or phenyl-substituted lower alkoxy substituent or a furyl group;

$R^2$ and $R^3$ both represent lower alkyl groups;

$R^4$ represents a hydrogen atom;

X represents a methylene group; and n is 2.

A more preferred class of compounds of the present invention are those compounds in which:

$R^1$ represents a $C_1$–$C_4$ alkoxy group, a $C_2$–$C_5$ alkenyl group, a $C_1$–$C_3$ alkyl group having a phenyl or phenoxy substituent, a phenyl group having a $C_1$–$C_4$ alkoxy or phenyl-substituted $C_1$–$C_3$ alkoxy substituent, or a furyl group;

$R^2$ represents a $C_1$–$C_3$ alkyl group;

$R^3$ represents a $C_1$–$C_5$ alkyl group;

$R^4$ represents a hydrogen atom;

X represents a methylene group; and n is 2.

A still more preferred class of compounds of the invention are those in which:

$R^1$ represents a $C_1$–$C_3$ alkoxy group, a $C_2$–$C_4$ alkenyl group, a $C_1$–$C_3$ alkyl group having a phenoxy substituent, a phenyl group having one or two $C_1$–$C_3$ alkoxy substituents or having a phenyl-substituted $C_1$–$C_3$ alkoxy substituent, or a furyl group;

$R^2$ represents a methyl group;

$R^3$ represents a $C_1$–$C_3$ alkyl group;

$R^4$ represents a hydrogen atom;

X represents a methylene group; and n is 2.

A still more preferred class of compounds of the present invention are those in which:

$R^1$ represents an ethoxy group, a $C_3$ alkenyl group, a phenoxyethyl group, a dimethoxyphenyl group, a phenyl group having a phenyl-substituted $C_1$ or $C_2$ alkoxy substituent, or a furyl group;

$R^2$ represents a methyl group;

$R^3$ represents a $C_1$–$C_3$ alkyl group;

$R^4$ represents a hydrogen atom;

X represents a methylene group; and n is 2.

The most preferred compounds of the invention are those in which:

$R^2$ and $R^3$ both represent methyl groups;

$R^4$ represents a hydrogen atom;

X represents a methylene group; and n is 2.

Examples of preferred compounds of formula (I) are given in the following list:

1. 4-[1-(3-Acetylthio-2-methylpropanoyl)prolyl]amino-6,7-dimethoxy-2-(4-methoxycarbonyl-1-piperazinyl)quinazoline
2. 4-[1-(3-Acetylthio-2-methylpropanoyl)prolyl]amino-2-(4-ethoxycarbonyl-1-piperazinyl)6,7-dimethoxyquinazoline
3. 4-[1-(3-Benzoylthio-2-methylpropanoyl)prolyl]amino-6,7-dimethoxy-2-(4-methoxycarbonyl-1-piperazinyl)quinazoline
4. 4-[1-(3-Benzoylthio-2-methylpropanoyl)prolyl]amino-2-(4-ethoxycarbonyl-1-piperazinyl)-6,7-dimethoxyquinazoline
5. 2-(4-Acetyl-1-piperazinyl)-4-[1-(3-acetylthio-2-methylpropanoyl)prolyl]amino-6,7-dimethoxyquinazoline
6. 4-[1-(3-Acetylthio-2-methylpropanoyl)prolyl]amino-6,7-dimethoxy-2-(4-propanoyl-1-piperazinyl)quinazoline
7. 4-[1-(3-Acetylthio-2-methylpropanoyl)prolyl]amino-2-(4-butanoyl-1-piperazinyl)-6,7-dimethoxyquinazoline
8. 4-[1-(3-Acetylthio-2-methylpropanoyl)prolyl]amino-6,7-dimethoxy-2(4-pentanoyl-1-piperazinyl)quinazoline
9. 4-[1-(3-Benzoylthio-2-methylpropanoyl)prolyl]amino-2-(4-butanoyl-1-piperazinyl)-6,7-dimethoxyquinazoline
10. 4-[1-(3-Benzoylthio-2-methylpropanoyl)prolyl]amino-6,7-dimethoxy-2-(4-pentanoyl-1-piperazinyl)quinazoline
11. 4-[1-(3-Acetylthio-2-methylpropanoly)prolyl]amino-2-(4-cyclopropanecarbonyl-1-piperazinyl)6,7-dimethoxyquinazoline
12. 4-[1-(3-Acetylthio-2-methylpropanoyl)prolyl]amino-2-(4-cyclobutanecarbonyl-1-piperazinyl)6,7-dimethoxyquinazoline
13. 4-[1-(3-Acetylthio-2-methylpropanoyl)prolyl]amino-2-(4-cyclopentanecarbonyl-1-piperazinyl)-6,7-dimethoxyquinazoline
14. 4-[1-(3-Acetylthio-2-methylpropanoyl)prolyl]amino-2-(4-cyclohexanecarbonyl-1-piperazinyl)-6,7-dimethoxyquinazoline
15. 4-[1-(3-Acetylthio-2-methylpropanoyl)prolyl]amino-2-(4-crotonoyl-1-piperazinyl)-6,7-dimethoxyquinazoline
16. 4-[1-(3-Acetylthio-2-methylpropanoyl)prolyl]amino-6,7-dimethoxy-2-[4-(2-pentenoyl)-1-piperazinyl]quinazoline
17. 4-[1-(3-Benzoylthio-2-methylpropanoyl)prolyl]amino-2-(4-crotonoyl-1-piperazinyl)6,7-dimethoxyquinazoline
18. 4-[1-(3-Benzoylthio-2-methylpropanoyl)prolyl]amino-6,7-dimethoxy-2-[4-(2-pentenoyl)-1-piperazinyl]quinazoline
19. 6,7-Dimethoxy-4-[1-(3-p-methylbenzoylthio-2-methylpropanoyl)prolyl]amino-2-[4-(2-pentenoyl)-1-piperazinyl]quinazoline
20. 4-[1-(3-Acetylthio-2-methylpropanoyl)prolyl]amino-2-(4-cyclopentylideneacetyl-1-piperazinyl)-6,7-dimethoxyquinazoline
21. 4-[1-(3-Acetylthio-2-methylpropanoyl)prolyl]amino-2-(4-cyclohexylideneacetyl-1-piperazinyl)-6,7-dimethoxyquinazoline
22. 4-[1-(3-Acetylthio-2-methylpropanoyl)prolyl]amino-6,7-dimethoxy-2-(4-phenylacetyl-1-piperazinyl)quinazoline
23. 4-[1-(3-Acetylthio-2-methylpropanoyl)prolyl]amino-6,7-dimethoxy-2-[4-(3-phenylpropanoyl)-1-piperazinyl]quinazoline
24. 4-[1-(3-Benzoylthio-2-methylpropanoyl)prolyl]amino-6,7-dimethoxy-2-(4-phenylacetyl-1-piperazinyl)quinazoline
25. 4-[1-(3-Benzoylthio-2-methylpropanoyl)prolyl]amino-6,7-dimethoxy-2-[4-(3-phenylpropanoyl)-1-piperazinyl]quinazoline
26. 4-[1-(3Acetylthio-2-methylpropanoyl)prolyl]amino-6,7-dimethoxy-2-(4-phenoxyacetyl-1-piperazinyl)quinazoline
27. 4-[1-(3-Acetylthio-2-methylpropanoyl)prolyl]amino-6,7-dimethoxy-2-[4-(2-phenoxypropanoyl)-1-piperazinyl]-quinazoline
28. 4-[1-(3-Benzoylthio-2-methylpropanoyl)prolyl]amino-6,7-dimethoxy-2-(4-phenoxyacetyl-1-piperazinyl)quinazoline
29. 4-[1-(3-Benzoylthio-2-methylpropanoyl)prolyl]amino-6,7-dimethoxy-2-[4-(2-phenoxypropanoyl)-1-piperazinyl]quinazoline
30. 6,7-Dimethoxy-4-[1-(3-p-methylbenzoylthio-2-methylpropanoyl)prolyl]amino-2-[4-(2-phenoxypropanoyl-1-piperazinyl]quinazoline
31. 4-[1-(3-Acetylthio-2-methylpropanoyl)prolyl]amino-6,7-dimethoxy-2-[4-(4-methoxybenzoyl)-1-piperazinyl]quinazoline
32. 4-[1-(3-Acetylthio-2-methylpropanoyl)prolyl]amino-2-[4-(3,4-dimethoxybenzoyl)-1-piperazinyl]-6,7-dimethoxyquinazoline
33. 4-[1-(3-Acetylthio-2-methylpropanoyl)prolyl]amino-6,7-dimethoxy-2-[4-(3,4,5-trimethoxybenzoyl)-1-piperazinyl]-quinazoline
34. 4-[1-(3-Benzoylthio-2-methylpropanoyl)prolyl]amino-2-[4-(3,4-dimethoxybenzoyl)-1-piperazinyl]-6,7- dimethoxyquinazoline
35. 4-[1-(3-Benzoylthio-2-methylpropanoyl)prolyl]amino-6,7-dimethoxy-2-[4-(3,4,5-trimethoxybenzoyl)-1-piperazinyl]quinazoline
36. 4-[1-(3-Acetylthio-2-methylpropanoyl)prolyl]amino-2-[4-(4-benzyloxybenzoyl)-1-piperazinyl]-6,7-dimethoxyquinazoline
37. 4-[1-(3-Acetylthio-2-methylpropanoyl)prolyl]amino-6,7-dimethoxy-2-[4-(1-phenylethoxy)benzoyl-1-piperazinyl]-quinazoline
38. 4-[1-(3-Acetylthio-2-methylpropanoyl)prolyl]amino-6,7-dimethoxy-2-[4-(1-methyl-1-phenylethoxy)benzoyl-1-piperazinyl]quinazoline
39. 4-1-(3-Benzoylthio-2-methylpropanoyl)-prolyl]amino-2-[4-(4-benzyloxybenzoyl)-1-piperazinyl]-6,7-dimethoxyquinazoline
40. 2-[4-(4-Benzyloxybenzoyl)-1-piperazinyl]-6,7-dimethoxy-4-[1-(3-propanoylthio-2-methylpropanoyl)prolyl]-aminoquinazoline.
41. 2-[4-(4-Benzyloxybenzoyl)1-piperazinyl]-6,7-dimethoxy-4-[1-(3-p-methylbenzoylthio-2-methylpropanoyl)prolyl]aminoquinazoline
42. 4-[1-(3-Benzoylthio-2-methylpropanoyl)prolyl]amino6,7-dimethoxy-2-[4-(4-1'-phenylethoxyben-zoyl)-1-piperazinyl]quinazoline
43. 4-[1-(3-Acetylthio-2-methylpropanoyl)prolyl]amino-2-[4-(2-furoyl)-1-piperazinyl]-6,7-dimethoxyquinazoline
44. 2-[4-(2-Furoyl)-1-piperazinyl]-6,7-dimethoxy-4-[1-(3-propanoylthio-2-methylpropanoyl)prolyl]aminoquinazoline 45. 4-[1-(3-Benzoylthio-2-methylpropanoyl)prolyl]amino-2-[4-(2-furoyl)-1-piperazinyl]-6,7-dimethoxyquinazoline
46. 2-[4-(2-Furoyl)-1-piperazinyl]-6,7-dimethoxy-4-[1-(3-p-methylbenzoylthio-2-methylpropanoyl)prolyl]aminoquinazoline
47. 4-[1-(3-Acetylthio-2-methylpropanoyl)prolyl]amino-6,7-dimethoxy-2-[4-oxazole-4-carbonyl)-1-piperazinyl]-quinazoline
48. 4-[1-(3-Acetylthio-2-methylpropanoyl)prolyl]amino-6,7-dimethoxy-2-[4-(5-methylthio-1,3,4-oxadiazole-2-carbonyl)-1-piperazinyl]quinazoline
49. 4-[1-(3-Benzoylthio-2-methylpropanoyl)prolyl]amino6,7-dimethoxy-2-[4-(5-methylthio-1,3,4-oxadiazole-2-carbonyl)-1-piperazinyl]quinazoline
50. 4-[1-(3-Acetylthio-2-methylpropanoyl)prolyl]amino-6,7-dimethoxy-2-[4-(2-tetrahydrofuroyl)-1-piperazinyl]quinazoline
51. 4-[1-(3-Benzoylthio-2-methylpropanoyl)prolyl]amino-6,7-dimethoxy-2-[4-(2-tetrahydrofuroyl)-1-piperazinyl]quinazoline
52. 4-[3-(3-Acetylthio-2-methylpropanoyl)thiazolidine-4-carbonyl]amino-6,7-dimethoxy-2-[4-(2-pentenoyl)-1-piperazinyl]quinazoline
53. 4-[3-(3-Benzoylthio-2-methylpropanoyl)thiazolidine-4-carbonyl]amino-6,7-dimethoxy-[4-(2-pentenoyl)-1-piperazinyl]quinazoline
54. 4-[3-(3-Acetylthiopropanoyl)thiazolidine-4-carbonyl]amino-2-8 4-cyclopentylideneacetyl-1-piperazinyl]-6,7-dimethoxyquinazoline
55. 4-[3-(3-Benzoylthiopropanoyl)thiazolidine-4-carbonyl]amino-2-(4-cyclohexylideneacetyl-1-piperazinyl]-6,7-dimethoxyquinazoline
56. 4-[3-(3-Benzoylthiopropanoyl)thiazolidine-4-carbonyl]amino-2-[4-(4-cinnamoyl-1-piperazinyl]-6,7-dimethoxyquinazoline
57. 4-[3-(3-Benzoylthiopropanoyl)thiazolidine-4-carbonyl]amino-2-[4-(4-methoxycinnamoyl)-1-piperazinyl]-6,7-dimethoxyquinazoline
58. 4-[3-(3-Benzoylthiopropanoyl)thiazolidine-4-carbonyl]amino-6,7-dimethoxy-2-[4-(3,4-methylenedioxycinnamoyl)-1-piperazinyl]quinazoline
59. 4-(3-(3-Benzoylthiopropanoyl)thiazoline-4-carbonyl]amino-6,7-dimethoxy-2-[4-phenylacetyl-1-piperazinyl]quinazoline
60. 4-[3-(3-Acetylthiopropanoyl)thiazolidine-4-carbonyl]amino-6,7-dimethoxy-2-[4-(2-phenoxypropanoyl)-1-piperazinyl]quinazoline
61. 4-[3-(3-Benzoylthiopropanoyl)thiazolidine-4-carbonyl]amino-6,7-dimethoxy-2-[4-(2-phenoxypropanoyl)-1-piperazinyl]quinazoline
62. 4-[3-(3-Benzoylthiopropanoyl)thiazolidine-4-carbonyl]amino-6,7-dimethoxy-2-[4-(3,4,5-trimethoxybenzoyl)-1-piperazinyl]quinazoline
63. 4-[3-(3-Benzoylthiopropanoyl)thiazolidine-4-carbonyl]amino-2[4-benzyloxybenzoyl)-1-piperazinyl]-6,7-dimethoxyquinazoline
64. 4-[3-(3-Benzoylthio-2-methylpropanoyl)thiazolidine-4-carbonyl]amino-2-[4-(4-benzyloxybenzoyl)-1-piperazinyl]-6,7-dimethoxyquinazoline
65. 4-[3-(3-Acetylthiopropanoyl)thiazolidine-4-carbonyl]amino-2-[4-(2-furoyl)-1-piperazinyl]-6,7-dimethoxyquinazoline
66. 4-[3-(3-Benzoylthiopropanoyl)thiazolidine-4-carbonyl]amino-2-[4-(2-furoyl)-1-piperazinyl]-6,7-dimethoxyquinazoline
67. 4-[2-(2-Acetoxyphenyl)-3-(3-benzoylthiopropanoyl)thiazolidine-4-carbonyl]amino-2-[4-(2-furoyl)-1-piperazinyl]-6,7-dimethoxyquinazoline
68. 4-[3-(3-Benzoylthio2-methylpropanoyl)thiazolidine-4-carbonyl]amino-2-[4-(2-furoyl)-1-piperazinyl]-6,7-dimethoxyquinazoline
69. 4-[3(3-Benzoylthiopropanoyl)thiazolidine-4-carbonyl]amino-6,7-dimethoxy-2-[4-(5-methylthio-1,3,4-oxadiazole-2-carbonyl)-1-piperazinyl]quinazoline
70. 4-[3-(3-Acetylthio-2-methylpropanoyl)thiazolidine-4-carbonyl]amino-2-(4-ethoxycarbonyl-1-piperazinyl)-6,7-dimethoxyquinazoline
70. 4-[3-(3-Benzoylthio-2-methylpropanoyl)thiazolidine-4-carbonyl]amino-2-(4-butyryl-1-homopiperazinyl)-6,7-dimethoxyquinazoline.

Of the compounds listed above, those numbered 2, 15, 27, 32, 36 and 43 are particularly preferred.

Because of the presence of a number of asymmetric carbon atoms, the compounds of the invention can exist in the form of various stereoisomers and, in particular, in the form of various optical isomers. Although these aare all represented by a single formula, it will be understood that the present invention envisages both the individual isomers and mixtures thereof. Of the preferred compounds of the invention, the following isomeric forms are most preferred:

4-[1-(D-3-Acetylthio-2-methylpropanoyl)-L-prolyl]amino-6,7-dimethoxy-2-[4-(2-phenoxypropanoyl)-1-piperazinyl]quinazoline;

4-[1-(D-3-Acetylthio-2-methylpropanoyl)-L-prolyl]amino-2-[4-(4-benzyloxybenzoyl)-1-piperazinyl]-6,7-dimethoxyquinazoline; and 4-[1-(D-3-Acetylthio-2-methylpropanoyl)-L-prolyl]amino-2-[4-(3,4-dimethoxybenzoyl)-1-piperazinyl]-6,7-dimethoxyquinazoline.

The compounds of the invention contain a number of electron-receptor nitrogen atoms and, accordingly, can form acid addition salts. The nature of the acid employed to form these salts is not critical, provided that it does not result in a substantial increase in toxicity of the salt as compared with the free base. The acid may be inorganic (e.g. hydrochloric acid, phosphoric acid, sulphuric acid or nitric acid) or organic (such as tartaric acid, citric acid, malic acid, lactic acid or maleic acid). The hydrochlorides are particularly preferred, in particular, the hydrochlorides of the compounds numbered 2, 15, 27, 32, 36 and 43 in the above list and the hydrochlorides of the preferred isomers listed above. The hydrochlorides and other salts can be prepared from the bases by conventional salification techniques.

The compounds of the invention may be prepared by reacting a 4-aminoquinazoline derivative of formula (II):

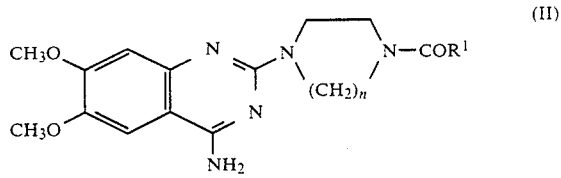

(in which $R^1$ and n are as defined above) with a carboxylic acid or formula (III):

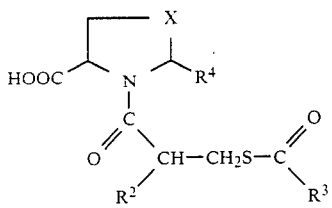

(in which R², R³, R⁴ and X are as defined above) or with a reactive derivative of said carboxylic acid. Although any of the conventional reactive derivatives of carboxylic acids may be used, the preferred reactive derivatives are monoalkyl and monoaryl esters of carbonic acids. The reaction is preferably effected in the presence of a solvent, the nature of which is not critical, provided that it has no adverse effect upon the reaction. Preferred solvents include: halogenated aliphatic hydrocarbons, such as methylene chloride or ethylene dichloride; ethers, such as tetrahydrofuran or dioxan; and esters, such as ethyl acetate. The reaction may be carried out over a wide temperature range, for example from −10° C. to 60° C., preferably from −5° C. to 40°. The time required for the reaction will vary, depending upon many factors, principally the reaction temperature, but the reaction will generally be complete within a period of from 5 to 20 hours.

The reagents are preferably employed in equimolar amounts or with an excess of said compound of formula (III) or its reactive derivative, more preferably the molar ratio of said compound of formula (II) to said compound of formula (III) or reactive derivative thereof is from 1 : 1 to 1 : 2.

The reaction can be made to proceed more smoothly by carrying it out in the presence of an acid-binding agent, which may be an organic base (for example triethylamine, N-methylmorpholine or 1,8-diazabicyclo[5.4.0]-undecene-5) or an inorganic base (such as an alkali metal carbonate or bicarbonate.

After completion of the reaction, the desired product may be recovered from the reaction mixture by conventional means. For example, the reaction mixture may be concentrated by evaporation under reduced pressure, after which the resulting residue is extracted with an organic solvent (for example chloroform or ethyl acetate), and then the solvent is distilled off from the extract to give the desired compound. This compound may, if necessary, be further purified by such conventional techniques as column chromatography or recrystallization.

The compounds of the invention are potent inhibitors of the activity of the angiotension I-converting enzyme and have excellent antihypertensive activities; they are thus effective for the prevention and treatment of various forms of hypertension, including essential hypertension, renal hypertension and adrenal hypertension. The inhibitory activities of the compounds of the invention are described hereinafter in the Examples, but it has, for example, been observed that the compounds of the invention can exhibit an antihypertensive activity of approximately from 20 to 80 mmHg at a dose of from 3 to 30 mg/kg (per os) in an antihypertension test using spontaneously hypertensive rats.

The compounds of the invention thus have good antihypertensive activities and may be used for the treatment of hypertension. The compounds are preferably administered orally, for example in the forms of tablets, capsules, powders, micro granules, granules, solutions or suspensions. Alternatively, they may be administered parenterally, preferably in the form of an injection or a suppository.

The preferred dose of the compounds of the invention will vary, depending upon the type and severity of the hypertension as well as upon the activity and duration of activity of the particular compound. In general, the daily dose, when the compound is administered orally, will be within the range of from 0.1 to 200 mg, preferably from 0.1 to 100 mg. For parenteral administration, a suitable dose is from one-third to one-tenth of the dose suggested for oral administration.

Although the compounds of the invention are quite effective by themselves for the treatment of various types of hypertension, they may also be used in conjunction with diuretics and other hypotensive agents, such as Γ-adrenergic receptor blocking agents.

The preparation of the compounds of the invention is further illustrated by the following non-limiting Examples.

EXAMPLE 1

4[1-(D-3-Acetylthio-2-methylpropanoyl)-L-prolyl-]amino-2-(4-ethoxycarbonyl-1-piperazinyl)-6,7-dimethoxy-quinazoline hydrochloride hemihydrate To 20 ml of chloroform were added 0.65 g of 1-(D3-acetylthio-2-methylpropanoyl)-L-proline and 0.5 g of triethylamine, and the resulting mixture was cooled with ice-water. 0.3 g of ethyl chloroformate was the added to the mixture, with stirring. After stirring the mixture for 30 minutes, 0.45 g of 4-amino-2-(4-ethoxycarbonyl-1-piperazinyl)-6,7-dimethoxy-quinazoline was added to the resulting mixture. The mixture was then stirred for 1 hour, with ice-cooling, and then for 15 minutes at room-temperature. The reaction mixture was then concentrated by evaporation under reduced pressure and the resulting residue was subjected to column chromatography through silica gel eluted with chloroform. 0.75 g of crystals were obtained from the eluate and these were dissolved in 5 ml of chloroform. 1 ml of 10% w/w hydrogen chloride/ethanol was then added to the solution and the resulting crystals were collected by filtration and recrystallized from 80 v/v aqueous ethanol, to give 0.7 g of the title compound in the form of a pale yellow powder melting at 208°–210° C. (with decomposition).

Elemental analysis:

Calculated for $C_{28}H_{38}N_6O_7S \cdot HCl \cdot 0.5H_2O$: C, 5189% H, 6.22% N, 12.97% Cl, 5.47%; S, 4.95%. Found: C, 52.03% H, 6.46%; N, 12.80%; Cl, 5.42%; S, 4.81%.

EXAMPLE 2

4[1-(D-3-Acetylthio-2-methylpropanoyl)-L-prolyl-]amino-2-(4-crotonoyl-1-piperazinyl)-6,7-dimethoxyquinazoline. hydrochloride hydrate To 20 ml of chloroform were added 0.7 g of 1-(D-3-acetylthio-2-methylpropanoyl)-L-proline and 0.5 g of triethylamine, after which the mixture was cooled with ice-water. 0.3 g of ethyl chloroformate was then added to the mixture, with stirring. The mixture was then stirred for 1 hour, after which 0.75 g of 4-amino-2-(4-crotonoyl-1-piperazinyl)-6,7-dimethoxy-quinazoline was added. The resulting mixture was stirred for 1 hour with ice-cooling and then for 14 hours at room temperature. At the end of this time, the reaction mixture was concentrated by evaporation under reduced pressure and the residue was subjected to column chromatography through silica gel eluted with 2% v/v ethanol/chloroform. 1.0 g of an oily substance was obtained from the eluate, and this was dissolved in 10 ml of chloroform. 1 ml of 10% w/w hydrogen chloride/ethanol was the added to the resulting solution and the crystals thus produced were collected by filtration and dried, to give 0.61 g of the desired compound in the form of a pale yellow powder melting at 204°–206° C. (with decomposition).

Elemental analysis:

Calculated for $C_{29}H_{37}N_6O_6S \cdot HCl \ H_2O$ C, 53.40% H, 6.18% N, 12.89% Cl, 4.92%; S, 5.44%. Found: C, 53.72%; H, 6.55% N, 13.02%; Cl, 5.25%, S, 5.05%.

EXAMPLE 3

4-[1-(D-3-Acetylthio-2-methylpropanoyl)-L-prolyl-]amino-6,7-dimethoxy-2[4-(2-phenoxypropionyl)-1-piperazinyl]quinazoline hydrochloride hydrate To 20 ml of chloroform were added 1.0 g of 1-(D-3-acetylthio-2-methylpropanoyl)-L-proline and 0.5 g of triethylamine, after which the mixture was cooled with ice-water. 0.36 g of ethyl chloroformate was added to the mixture, with stirring. After the mixture had been stirred for 30 minutes, 0.90 g of 4-amino-6,7-dimethoxy-2-[4-(2-phenoxypropionyl)-1-piperazinyl]-quinazoline was added. The resulting mixture was stirred, with ice-cooling, for 30 minutes and then at room temperature for 20 hours. The mixture was then concentrated by evaporation under reduced pressure and the residue was subjected to column chromatography through silica gel eluted with chloroform. 1.0 g of a glassy substance was obtained from the eluate. This substance was dissolved in 10 ml of chloroform, and then 1 ml of 10% w/w hydrogen chloride/ethanol was added to the resulting solution. The resulting precipitate was dried, giving 0.70 g of the title compound in the form of a pale yellow powder melting at 198°–200° C. (with decomposition).

Elemental analysis:

Calculated for $C_{34}H_{41}N_6O_7S \ HCl \ H_2O$: C, 55.76%; H, 6.06%; N, 11.48%; Cl, 4.84%; S, 4.38%. Found: C, 55.71%; H, 6.13%; N, 11.48%; Cl, 4.74%; S, 4.70%.

EXAMPLE 4

4-[1-(D-3-Acetylthio-2-methylpropanoyl)-L-prolyl-]amino-2-[4-(4-benzyloxybenzoyl)-1-piperazinyl]-6,7-dimethoxy-quinazcline hydrochloride sesquihydrate To 20 ml of chloroform were added 0.71 g of 1-(D-3-acetylthio-2-methylpropanoyl)-L-proline and 0.5 g of triethylamine, after which the mixture was cooled with ice-water. 0.3 g of ethyl chloroformate was added, with stirring, and then the mixture was stirred for a further 20 minutes. At the end of this time, 10 ml of a chloroform solution containing 1.15 g of 4-amino-2-[4-(4-benzyloxybenzoyl)-1-piperazinyl]-6,7-dimethoxyquinazoline were added. The mixture was then stirred for 1 hour with ice-cooling and then for 15 hours at room temperature. At the end of this time, the reaction mixture was concentrated by evaporation under reduced pressure and the resulting residue was subjected to column chromatography through silica gel eluted with 2% v/v ethanol/chloroform, to give 1.2 g of a viscous substance, which was dissolved in a small quantity of chloroform. 1 ml of 10% w/w hydrogen chloride/ethanol was added to the resulting solution and the crystals thus produced were collected by filtration, to give 0.95 g of the title compound in the form of pale yellow needles melting at 182°–186° C.

Elemental analysis:

Calculated for $C_{39}H_{44}N_6O_7S \ HCl \ 1.5H_2O$: C, 58.24%; H, 6.01%; N, 10.45%; Cl, 4.41%; S, 3.99%. Found: C, 58.37%; H 5.67%, N, 10.51%; Cl, 4.23%; S, 4.20%.

EXAMPLE 5

4-[1-(D-3-Acetylthio-2-methylpropanoyl)-L-prolyl-]amino-2-(4-(3,4-dimethoxybenzoyl)-1-piperazinyl]-6,7-dimethoxy-quinazoline hydrochloride sesquihydrate To 20 ml of chloroform were added 0.7 g of 1-(D-3-acetylthio-2-methylpropanoyl)-L-proline and 0.5 g of triethylamine, after which the mixture was cooled with ice-water. 0.4 g of phenyl chloroformate was then added to the mixture, with stirring, after which the mixture was stirred for a further 30 minutes. 0.8 g of 4-amino-2-[4-dimethoxybenzoyl)-1-piperazinyl]-6,7-dimethoxyquinazoline was then added to the mixture, after which it was stirred for 1 hour with ice-cooling and then for 20 hours at room temperature. The reaction mixture was then concentrated by evaporation under reduced pressure and the resulting residue was subjected to column chromatography through silica gel eluted with 2% v/v ethanol/chloroform, to give 0.95 g of a glassy substance. This was dissolved in 10 ml of chloroform, and 1ml of 10% w/w hydrogen chloride/ethanol was added to the solution. The resulting crystals were collected by filtration, to give 0.50 g of the title compound in the form of pale yellow needles melting at 180°–185° C. (with decomposition).

Elemental analysis:

Calculated for $C_{34}H_{41}N_6O_8S \ HCl \ 1.5H_2O$: C, 53.92%; H, 5.99%; N, 11.10%; Cl, 4.23%; S, 4.68%. Found: C, 54.04%; H, 5.88%; N, 11.45%; Cl, 4.46%; S, 4.66%.

EXAMPLE 6

4-[3-(DL-3-Acetylthio-2-methylpropanoyl)thiazolidine-4-carbonyl]amino-2-(4-ethoxycarbonyl-1-piperazinyl)-6,7-dimethoxyquinazoline hydrochloride hemihydrate To 20 ml of chloroform were added 0.50 g of 3-(DL-3-acetylthio-2-methylpropanoyl)thiazolidine-4-carboxylic acid and 0.50 g of triethylamine, after which the mixture was cooled with ice-water. To the mixture was added, with stirring, 0.20 g of ethyl chloroformate. The mixture was then stirred for a further 30 minutes after which 0.50 g of 4-amino-2-(4-ethoxycarbonyl-1-piperazinyl)-6,7-dimethoxyquinazoline was added. The resulting mixture was stirred for 1 hour with ice-cooling and then for 15 hours at room temperature. The mixture was then concentrated by evaporation under reduced pressure and the resulting residue was subjected to column chromatography through silica gel eluted with 1% v/v ethanol/chloroform, to give 0.30 g of a glassy substance. This was dissolved in 5 ml of chloroform, and 1ml of 10% w/w hydrogen chloride/ethanol was added to the solution, after which the resulting precipitate was separated, to give 0.21 g of the title compound in the form of pale yellow needles melting at 203°–205° C. (with decomposition).

Elemental analysis:

Calculated for $C_{27}H_{36}N_6O_7S_2 \ HCl \ 0.5H_2O$:

C, 48.68%; H, 5.75%; N, 12.61%; Cl, 5.32%; S, 9.63%;.

Found: C, 48.57%; H, 5.68%; N, 12.44%; Cl, 5.14%; S, 9.83%.

EXAMPLE 7

4-[1-(D-3-Acetylthio-2-methylpropanoyl)-L-prolyl-]amino-2-[4-(2-furoyl)-1-piperazinyl]-6,7-dimethoxyquinazoline.hydrochloride.hydrate To 20 ml of chloroform were added 1.2 g of 1-(D-3-acetylthio-2-methylpropanoyl)-L-proline and 1.0 g of triethylamine, after which the mixture was cooled with ice-water. 0.6 g of ethyl chloroformate was then added, with stirring, to the resulting mixture, which was then stirred for a further 1 hour. At the end of this time, 0.85 g of 4-amino-2-[4-(2-furoyl)-1-piperazinyl]-6,7-dimethoxyquinazoline was added and the resulting mixture was stirred for 1 hour with ice-cooling and then for 14 hours at room temperature. The reaction mixture was then concentrated by evaporation under reduced pressure and the residue was subjected to column chromatography through silica gel eluted with 2% v/v ethanol/chloroform to give 1.35 g of an oily substance. This substance was dissolved in 20 ml of chloroform, and 1 ml of 10% w/w hydrogen chloride/ethanol was added thereto. The crystals thus produced were recrystallized from 50% v/v aqueous ethanol, to give 0.90 g of the title compound in the form of pale yellow needles melting at 215°–217° C. (with decomposition).

Elemental analysis: Calculated for $C_{30}H_{36}N_6O_7S \cdot HCl \cdot H_2O$: C, 53.05%; H, 5.79%; N, 12.37%; Cl, 5.22%; S, 4.72%. Found: C, 52.83%; H, 5.55%; N, 12.39%; Cl, 5.25%; S, 4.94%.

Measurement of inhibitory activity against the angiotension I-converting enzyme

The inhibitory activities of compounds of the invention and of the known compound, prazosin, against the angiotension I-converting enzyme (ACE) were measured by the method of D. W. Cushman and H. S. Cheung [Biochem. Pharmacol. 20, 637 (1971)], using hippuryl-l-histidyl-l-leucine as a substrate. The reaction mixture consisted of 225 μl of a 0.1 M borate buffer solution (pH 8.3) containing 0.4 M sodium chloride, 25 μl of the substrate (12.5 mM solution), 25 μl of a partially purified ACE and 25 μl of a test compound solution (prepared from a 1 mg/ml aqueous acetone solution of the compound). This reaction mixture was maintained at 37° C. for 30 minutes, after which 300 μl of 1N hydrochloric acid were added in order to stop the reaction. 2 ml of ehtyl acetate were then added and the mixture was stirred for 10 seconds and then centrifuged at 3,000 rpm for 5 minutes. 1.5 ml of the ethyl acetate layer was separated and concentrated by evaporation to dryness. The residue was dissolved in 1 ml of distilled water and the quantity of hippuric acid in this solution was measured from its absorbance at 228 mμ, using a spectrophotometer.

The ACE solution was prepared by homogenizing 5 g of acetone powders of rabbit lungs (a product of Sigma Chemical Co., U.S.A., prepared by homogenizing rabbit lungs in a buffer solution and separating out the enzymes precipitated with acetone) in 50 ml of a borate buffer solution (pH 8.3), centrifuging the mixture at 40,000 G for 30 minutes and then separating the supernatant.

The inhibitory activity against ACE was calculated from the formula:

$$\text{Inhibitory activity} = \frac{A_c - A_s}{A_c} \times 100\ (\%)$$

in which $A_c$ is the absorbance of the control and $A_s$ is the absorbance of the sample. Inhibition curves were made for each sample by measuring the inhibitory activity at five different concentrations, prepared by two-fold dilutions. The $IC_{50}$ values, which are the molar concentrations of the compounds required to inhibit the ACE activity by 50%, were calculated for each compound. The results are shown in the following Table.

TABLE

| Compound (Example No.) | Inhibitory concentration $IC_{50}$ (M) |
| --- | --- |
| 1 | $4.16 \times 10^{-7}$ |
| 2 | $3.60 \times 10^{-7}$ |
| 3 | $3.41 \times 10^{-7}$ |
| 4 | $4.45 \times 10^{-7}$ |
| 5 | $2.61 \times 10^{-7}$ |
| 6 | $1.41 \times 10^{-6}$ |
| 7 | $3.10 \times 10^{-7}$ |
| prazosin | $\geq 1 \times 10^{-5}$ |

We claim:
1. An acylaminoquinazoline compound of formula (I):

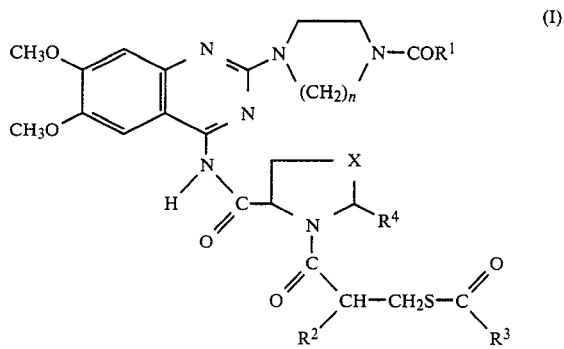

in which:
R[1] represents lower alkoxy, lower alkyl, $C_3$–$C_7$ cycloalkyl, lower alkenyl, vinyl having a phenyl or furyl substituent, said phenyl substituent being unsubstituted or having one substituent selected from lower alkoxy and methylenedioxy, lower alkyl having one substituent selected from phenyl, phenoxy and cycloalkylidene having 3 to 7 carbon atoms, phenyl which is unsubstituted or has 1–3 substituents selected from lower alkoxy and phenyl-substituted lower alkoxy, furyl, oxazolyl, methylthiooxadiazolyl or tetrahydrofuryl;

R[2] represents a hydrogen atom or lower alkyl;

R[3] represents lower alkyl or phenyl which is unsubstituted or has one substituent selected from lower alkyl, lower alkoxy and halogen atoms;

R[4] represents a hydrogen atom or $C_2$–$C_4$ alkylcarbonyloxy-substituted phenyl;

X represents methylene or sulphur; and n is 2 or 3, and pharmaceutically acceptable acid addition salts thereof.

2. The compound as claimed in claim 1, wherein:

$R^1$ represents lower alkoxy, lower alkenyl, lower alkyl having one substituent selected from phenyl groups and phenoxy, phenyl having 1–3 substituents selected from lower alkoxy and phenyl-substituted lower alkoxy, or furyl;

$R^2$ and $R^3$ each represent lower alkyl;

$R^4$ represents a hydrogen atom;

X represents methylene; and n is 2, and pharmaceutically acceptable acid addition salts thereof.

3. The compound as claimed in claim 1, wherein:

$R^1$ represents $C_1$–$C_4$ alkoxy, $C_2$–$C_5$ alkenyl, $C_1$–$C_3$ alkyl having one substituent selected from phenyl and phenoxy, phenyl having 1–3 substituents selected from $C_1$–$C_4$ alkoxy and phenyl-substituted $C_1$–$C_3$ alkoxy, or furyl;

$R^2$ represents $C_1$–$C_3$ alkyl;

$R_3$ represents $C_1$–$C_5$ alkyl;

$R^4$ represents a hydrogen atom;

X represents methylene; and n is 2, and pharmaceutically acceptable acid addition salts thereof.

4. The compound as claimed in claim 1, wherein:

$R^1$ represents $C_1$–$C_3$ alkoxy, $C_2$–$C_4$ alkenyl, phenoxy-substituted $C_1$–$C_3$ alkyl, phenyl having one or two $C_1$–$C_3$ alkoxy substituents, phenyl having a phenyl-substituted $C_1$–$C_3$ alkoxy substituent, or furyl;

$R^2$ represents methyl;

$R^3$ represents $C_1$–$C_3$ alkyl;

$R^4$ represents a hydrogen atom;

X represents methylene; and n is 2, and pharmaceutically acceptable acid addition salts thereof.

5. The compound as claimed in claim 1, wherein:

$R^1$ represents ethoxy, $C_3$ alkenyl, phenoxy-substituted ethyl, phenyl having two methoxy substituents, phenyl having a phenyl-substituted $C_1$ or $C_2$ alkoxy substituent, or furyl;

$R^2$ represents methyl;

$R^3$ represents $C_1$–$C_3$ alkyl;

$R^4$ represents a hydrogen atom;

X represents methylene; and n is 2, and pharmaceutically acceptable acid addition salts thereof.

6. The compound as claimed in claim 1, wherein:

$R^2$ and $R^3$ each represents methyl, $R_4$ represents a hydrogen atom, X represents methylene and n is 2, and pharmaceutically acceptable acid addition salts thereof.

7. The compounds as claimed in claim 1, selected from the group consisting of:

4-[1-(3-Acetylthio-2-methylpropanoyl)prolyl]amino-2-(4-ethoxycarbonyl-1-piperazinyl)-6,7-dimethoxyquinazoline, 4-[1-(3-Acetylthio-2-methylpropanoyl)prolyl]amino-2-(4-crotonoyl-1-piperazinyl)-6,7-dimethoxyquinazoline, 4-[1-(3-Acetylthio-2-methylpropanoyl)prolyl]amino-6,7-dimethoxy-2-[4-(2-phenoxypropanoyl)-1-piperazinyl]quinazoline, 4-[1-(3-Acetylthio-2-methylpropanoyl)prolyl]amino-2-[4-(3,4-dimethoxybenzoyl)-1-piperazinyl]6,7-dimethoxyquinazoline, 4-[1-(3-Acetylthio-2-methylpropanoyl)prolyl]amino-2-[4-(4-benzyloxybenzoyl)-1-piperazinyl]-6,7-dimethoxyquinazoline, 4-[1-(3-Acetylthio-2-methylpropanoyl)prolyl]amino-2-[4-(2-furoyl)-1-piperazinyl]-6,7-dimethoxyquinazoline, and the hydrochlorides thereof.

8. 4-[1-(D-3-Acetylthio-2-methylpropanoyl)-L-prolyl]amino-6,7-dimethoxy-2-[4-(2-phenoxypropanoyl)-1-piperazinyl]quinazoline and its hydrochloride.

9. 4-[1-(D-3-Acetylthio-2-methylpropanoyl)-L-prolyl]amino-2-[4-(4-benzyloxybenzoyl)-1-piperazinyl]-6,7-dimethoxyquinazoline and its hydrochloride.

10. 4-[1-(D-3-Acetylthio-2-methylpropanoyl)-L-prolyl]amino-2-[4-(3,4-dimethoxybenzoyl)-1-piperazinyl]-6,7-dimethoxyquinazoline and its hydrochloride.

11. The compound of claim 1 wherein when $R_1$ is substituted phenyl and (i) when said phenyl is monosubstituted, said substituent is in the 2, 3 or 4 position, (ii) when said phenyl is disubstituted, said substituents are in the 3 and 4 positions, and (iii) when said substituent is trisubstituted, said substituents are in the 3, 4 and 5 positions.

12. A pharmaceutical composition for the treatment of hypertension, comprising an effective amount of an antihypertensive agent in admixture with a pharmaceutically acceptable carrier or diluent, wherein said antihypertensive agent is selected from compounds of formula (I):

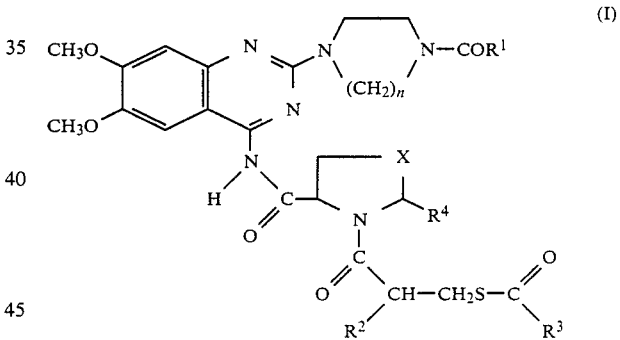

in which:

$R^1$ represents lower alkoxy, lower alkyl, $C_3$–$C_7$ cycloalkyl, lower alkenyl, vinyl having a phenyl or furyl substituent, said phenyl substituent being unsubstituted or having one substituent selected from lower alkoxy and methylenedioxy, lower alkyl having one substituent selected from phenyl, phenoxy and cycloalkylidene having 3 to 7 carbon atoms, phenyl which is unsubstituted or has 1–3 substituents selected from lower alkoxy and phenyl-substituted lower alkoxy, furyl, oxazolyl, methylthiooxadiazolyl or tetrahydrofuryl;

$R^2$ represents a hydrogen atom or lower alkyl;

$R^3$ represents lower alkyl or phenyl which is unsubstituted or has one substituent selected from lower alkyl, lower alkoxy and halogen atoms;

$R^4$ represents a hydrogen atom or $C_2$–$C_4$ alkylcarbonyloxy-substituted phenyl;

X represents methylene or sulphur; and n is 2 or 3, and pharmaceutically acceptable acid addition salts thereof.

13. The pharmaceutical composition as claimed in claim 12, wherein:
   $R^1$ represents lower alkoxy, lower alkenyl, lower alkyl having one substituent selected from phenyl and phenoxy, phenyl having 1-3 substituents selected from lower alkoxy and phenyl-substituted lower alkoxy, or furyl;
   $R^2$ and $R^3$ each represent lower alkyl;
   $R^4$ represents a hydrogen atom;
   X represents methylene; and
   n is 2.

14. The pharmaceutical composition as claimed in claim 12, wherein:
   $R^1$ represents $C_1$–$C_4$ alkoxy, $C_2$–$C_5$ alkenyl, $C_1$–$C_3$ alkyl having one substituent selected from phenyl and phenoxy, phenyl having 1-3 substituents selected from $C_1$–$C_4$ alkoxy and phenyl-substituted $C_1$–$C_3$ alkoxy, or furyl;
   $R^2$ represents $C_1$–$C_3$ alkyl;
   $R^3$ represents $C_1$–$C_5$ alkyl;
   $R^4$ represents a hydrogen atom;
   X represents methylene; and
   n is 2.

15. The pharmaceutical composition as claimed in claim 12, wherein:
   $R^1$ represents $C_1$–$C_3$ alkoxy, $C_2$–$C_4$ alkenyl, phenoxy-substituted $C_1$–$C_3$ alkyl, phenyl having one or two $C_1$–$C_3$ alkoxy substituents, phenyl having a phenyl-substituted $C_1$–$C_3$ alkoxy substituent, or furyl;
   $R^2$ represents methyl;
   $R^3$ represents $C_1$–$C_3$ alkyl;
   $R^4$ represents a hydrogen atom;
   X represents methylene; and
   n is 2.

16. The pharmaceutical composition as claimed in claim 12, wherein:
   $R^1$ represents ethoxy, $C_3$ alkenyl, phenoxy-substituted ethyl, phenyl group having two methoxy substituents, phenyl having a phenyl-substituted $C_1$ or $C_2$ alkoxy substituent, or furyl;
   $R^2$ represents methyl;
   $R^3$ represents $C_1$–$C_3$ alkyl;
   $R^4$ represents a hydrogen atom;
   X represents methylene; and
   n is 2.

17. The pharmaceutical composition as claimed in claim 12, wherein $R^2$ and $R^3$ each represents methyl, $R^4$ represents a hydrogen atom, X represents methylene and n is 2.

18. The pharmaceutical composition as claimed in claim 12, wherein said antihypertensive agent is selected from the group consisting of:
   4-[1-(3-Acetylthio-2-methylpropanoyl)prolyl]amino-2-(4-ethoxycarbonyl-1-piperazinyl)-6,7-dimethoxyquinazoline,
   4-[1-(3-Acetylthio-2-methylpropanoyl)prolyl]amino-2-(4-crotonoyl-1-piperazinyl)-6,7-dimethoxyquinazoline,
   4-[1-(3-Acetylthio-2-methylpropanoyl)prolyl]amino-6,7-dimethoxy-2-[4-(2-phenoxypropanoyl)-1-piperazinyl]quinazoline,
   4-[1-(3-Acetylthio-2-methylpropanoyl)prolyl]amino-2-[4-(3,4-dimethoxybenzoyl)-1-piperazinyl]-6,7-dimethoxyquinazoline,
   4-[1-(3-Acetylthio-2-methylpropanoyl)prolyl]amino-2-[4-(4-benzyloxybenzoyl)-1-piperazinyl]-6,7-dimethoxyquinazoline,
   4-[1-(3-Acetylthio-2-methylpropanoyl)prolyl]amino-2-[4-(2-furoyl)-1-piperazinyl]-6,7-dimethoxyquinazoline,
   and the hydrochlorides thereof.

19. The pharmaceutical composition as claimed in claim 12, wherein said antihypertensive agent is selected from the group consisting of:
   4-[1-(D-3-Acetylthio-2-methylpropanoyl)-L-prolyl]amino-6,7-dimethoxy-2-[4-(2-phenoxypropanoyl)-1-piperazinyl]quinazoline,
   4-[1-(D-3-Acetylthio-2-methylpropanoyl)-L-prolyl]amino-2-[4-(4-benzyloxybenzoyl)-1-piperazinyl]-6,7-dimethoxyquinazoline,
   4-[1-(D-3-Acetylthio-2-methylpropanoyl)-L-prolyl]amino-2-[4-(3,4-dimethoxybenzoyl)-1-piperazinyl]-6,7-dimethoxyquinazoline,
   and the hydrochlorides thereof.

20. The pharmaceutical composition of claim 12 wherein when $R_1$ is substituted phenyl, and (i) when said phenyl is monosubstituted, said substituent is in the 2, 3 or 4 position, (ii) when said phenyl is disubstituted, said substituents are in the 3 and 4 positions, and (iii) when said substituent is trisubstituted, said substituents are in the 3, 4 and 5 positions.

* * * * *